United States Patent [19]
Hurley et al.

[11] Patent Number: 5,209,734
[45] Date of Patent: May 11, 1993

[54] CONTINUOUS SPINAL ANESTHESIA ADMINISTERING APPARATUS

[75] Inventors: Ronald J. Hurley, Norwell, Mass.; Kenneth W. Larson, Keene, N.H.; Douglas F. Reed, Lithonia, Ga.; Donald H. Lambert, Westwood, Mass.

[73] Assignee: Brigham and Women's Hospital, Inc., Boston, Mass.

[21] Appl. No.: 576,455

[22] PCT Filed: Mar. 21, 1989

[86] PCT No.: PCT/US89/01172
§ 371 Date: Dec. 19, 1990
§ 102(e) Date: Dec. 19, 1990

[51] Int. Cl.$^5$ .................. A61M 5/178; A61M 25/00
[52] U.S. Cl. ........................................ 604/158; 604/282
[58] Field of Search .............. 604/51, 164, 158, 170, 604/256, 280, 282, 264; 128/772, 657, 658

[56] References Cited

U.S. PATENT DOCUMENTS

| | | | |
|---|---|---|---|
| 2,268,321 | 12/1941 | Flynn | 604/282 |
| 3,757,768 | 9/1973 | Kline | 128/657 |
| 3,922,378 | 1/1975 | Kline | 427/2 |
| 4,239,042 | 12/1980 | Asai | 604/282 X |
| 4,385,635 | 5/1983 | Ruiz | 128/658 |
| 4,737,146 | 4/1988 | Amaki et al. | 604/51 |
| 4,739,768 | 4/1988 | Engelson | 128/658 |
| 4,764,324 | 8/1988 | Burnham | 264/103 |
| 4,917,670 | 4/1990 | Hurley et al. | 604/51 |
| 4,985,022 | 1/1991 | Fearnot et al. | 604/282 |
| 5,078,702 | 1/1992 | Pomeranz | 604/280 |

OTHER PUBLICATIONS

Catalog Description "Bizarri—Giuffrida Set for Continuous Spinal anesthesia" Manufactured by Becton—Dickinson, 3 pages, 1983.

*Primary Examiner*—John D. Yasko
*Assistant Examiner*—Adam J. Cermak
*Attorney, Agent, or Firm*—David G. Conlin; Henry D. Pahl, Jr.

[57] ABSTRACT

A continuous spinal anesthesia administering apparatus is disclosed which comprises a polymeric microcatheter with a reinforcing stylet. A method for administering anesthesia to a patient utilizing this apparatus is also disclosed, as is a catheter kit containing this apparatus.

30 Claims, 4 Drawing Sheets

CONTINUOUS SPINAL ANESTHESIA ADMINISTERING APPARATUS

BACKGROUND OF THE INVENTION

This invention relates to continuous spinal anesthesia and particularly to an improved apparatus through which the anesthesia is administered.

Continuous spinal anesthesia has become a widely recognized technique in the last two decades, having been described by a variety of practitioners including Bizzari et al (*Anesthesia and Analgesia*, 43: 393, 1964), Giuffrida et al (*Anesthesia and Analgesia*. 51: 117, 1972), and Shroff et al (*Southern Medical Journal*, 81: 178, 1988), among others. In the techniques described heretofore, generally a 17 to 21 gauge spinal needle was used to puncture the lumbar dura at the desired interspace (L2-3 or L3-4) so as to enter the subarachnoid space, then a flexible catheter (about 20 gauge or 0.81 mm O.D. to about 23 gauge or 0.56 mm O.D.) reinforced with a metal stylet was inserted through the needle, the needle and stylet were withdrawn leaving the catheter in place, and anesthetic was administered through the catheter as required.

Continuous spinal anesthesia as described above has been recognized to provide a number of advantages over single dose injection including accurate control of the level and duration of anesthesia, induction of anesthesia with the patient in the operative position, the use of minimal doses of anesthetic, and the use of short acting anesthetics. In spite of these recognized advantages, however, the continuous technique has not been widely used by practitioners. One apparent reason for this lack of acceptance, among several postulated, is that the incidence of postdural puncture headache is sufficiently high to cause concern.

Postdural puncture headache is primarily attributable to the size of the needle used and incidence of headache decreases as the needle size decreases. Thus, the standard 25 or 26 gauge needle utilized in single injection spinal anesthesia produces a relatively low incidence of headache, while the larger 18 to 20 gauge needle required for continuous spinal anesthesia (the needle must be large enough to allow the catheter to pass through) produces a much greater incidence of headache. This disadvantage has thus prevented greater acceptance of the continuous spinal anesthesia technique.

In U.S. Pat. No. 3,780,733, an effort was made to overcome this disadvantage by coupling a 25 gauge needle to the end of a standard 20 gauge catheter and piercing the dura wall, so as to reach the subarachnoid space, only with this small gauge needle. To accomplish this, a larger 15 gauge needle was first partially inserted into the extradural space to act as a guide for the smaller catheter/needle unit. Then, the smaller catheter/needle unit was introduced through the lumen of the larger needle until it penetrated the subarachnoid space with assistance from a stylet inserted in the catheter.

While presumably the apparatus and technique disclosed in the above described patent would achieve a reduction in the incidence of postdural puncture headache, it is believed that the apparatus contemplated would be difficult to manufacture and would raise additional concerns that would detract from its use. One such concern would be the permanence of the coupling connecting the small needle to the catheter. If the needle could be accidentally dislodged while in the patient, the result could be disastrous. A second concern would be the maintenance of a sharp metal needle in the subarachnoid space during surgery. Any unnecessary movement of the needle could cause damage beyond the initial puncture. Neither of these concerns is present if only a flexible, one piece polymeric catheter is inserted in the subarachnoid space.

SUMMARY OF THE INVENTION

The present invention provides a continuous spinal anesthesia administering apparatus which reduces the incidence of postdural puncture headache to an almost negligible level, while avoiding the introduction of any countervailing problems that would detract from its use. The apparatus of the present invention comprises a polymeric microcatheter having an external diameter less than about 0.0120 inch (0.305 mm), so that it will fit through a thin wall 24 to 26 gauge spinal needle, with a reinforcing stylet inserted therein. This apparatus may be utilized for the continuous administration of spinal anesthesia to a patient by inserting a hollow surgical needle of about 24 to 26 gauge partially into the desired spinal site, inserting the apparatus of the present invention (i.e. microcatheter with stylet) into said needle and advancing it until it has projected beyond the needle opening and into the desired spinal site (subarachnoid space), administering anesthetic to the patient through the microcatheter as desired.

DETAILED DESCRIPTION OF THE INVENTION

The continuous spinal anesthesia technique to which this invention applies is one that is currently known in the medical profession and described in the Background of the Invention, as well as in the references cited therein. In general terms, this technique involves first selecting an appropriate interspinous vertebral space, such as the L2-3 or L3-4 interspace, and inserting a spinal needle until it partially enters the subarachnoid space. A flexible catheter reinforced with a metal stylet is inserted through the needle until the end of the catheter projects beyond the tip of the needle a few centimeters into the subarachnoid space. The needle is then carefully withdrawn from the patient, leaving the catheter in place. Anesthetic may then be administered through the catheter as required to achieve the desired spinal blockade. The stylet may be maintained within the microcatheter during infusion of the anesthetic provided that there is sufficient clearance between the stylet and the microcatheter internal wall to allow a sufficient volume of anesthetic to pass through. The anesthetic is generally delivered to the catheter via a syringe connected through an adapter to the catheter The present invention provides a substantial improvement in the continuous administration of spinal anesthesia that has not been heretofore possible. This improvement is achieved through the use of a very small gauge spinal needle and a very small gauge microcatheter with reinforcing stylet.

The spinal needle which is utilized in the anesthetic technique of the present invention may be any of those currently available for single dose spinal blockade The spinal needle will thus be about 24 gauge (0.508 mm O.D.) or smaller with an interior lumen of sufficient size to accept the microcatheter described below. Preferably the spinal needle will be between about 24 gauge and about 26 gauge (0.403 mm O.D.), and most preferably about 25 gauge (0.454 mm O.D.). A thin walled spinal needle, such as the Beckton-Dickinson disposable spinal needle with Quinke point, is particularly advantageous since it has a relatively large lumen through which the microcatheter can be easily inserted. Generally, suitable spinal needles will carry the designation thin wall, extra thin wall or ultra thin wall and such needles are readily available to the medical profession.

Figure 1:
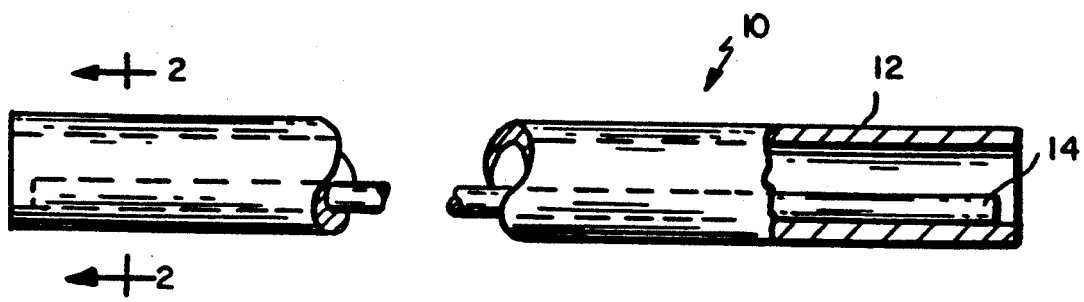
FIG. 1 is a fragmentary side view, partially in section, of a microcatheter and supporting stylet in accordance with the present invention.
Figure 2:
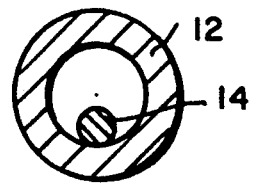
FIG. 2 is a sectional view, taken along lines 2—2 in FIG. 1.

In the drawings, FIGS. 1 and 2 show the continuous medicament administering apparatus 10, which comprises microcatheter 12 and stylet 14.

A particularly important feature of the present invention is the microcatheter which is employed This microcatheter is a small gauge, thin-walled microcatheter tube which is capable of being inserted within the previously described small gauge spinal needle and yet it is of sufficient interior diameter so as to provide a sufficient flow rate for proper administration of anesthetic.

This microcatheter can be made of any flexible, nontoxic, biocompatible polymeric material. Such polymeric materials may include, but are not limited to, polyimides, polyamides, polyamide-imides, fluoropolymers, polyurethanes, and polyolefins, as well as such materials containing various fillers to impart desirable properties. The polymeric microcatheter may also contain layers of other biocompatible materials therewithin such as metal or silica as desired to impart particular properties. Thus, the term polymeric should not be strictly interpreted to include only organic homopolymers or copolymers, but rather any material with a polymeric component.

The polymeric microcatheter should have an external diameter less than about 0.0130 inch (0.330 mm), that is, about 29 gauge or smaller. Preferably, the microcatheter will have an external diameter of about 0.0085 inch (0.216 mm or 33 gauge) to about 0.0107 inch (0.272 mm or 31 gauge). The microcatheter should have an internal diameter greater than about 0.0065 inch (0.165 mm) and preferably between about 0.0071 inch (0.180 mm) and about 0.0091 inch (0.230 mm). Most preferably the microcatheter will have an external diameter of about 0.0094 inch (0.238 mm or 32 gauge) and an internal diameter of about 0.0079 inch (0.200 mm). The microcatheter may advantageously contain markings, either visible or radio-opaque, or may itself be radio-opaque to help identify the position of the microcatheter upon insertion into the patient A particularly preferred microcatheter for use in the present invention, and one that is currently available and suitable for this use, is a thin walled aromatic polyimide tube manufactured by Hudson Viking Corporation of Trenton, Ga. and Polymicro Technologies Inc. of Pheonix, Ariz. The 32 gauge tube is most preferred.

An important feature of the present invention is the reinforcing stylet, without which it would be difficult or impossible to thread the microcatheter through the spinal needle. The stylet also prevents occlusions in the microcatheter. This stylet must have an outside diameter small enough to enable it to fit within the microcatheter. Thus, the stylet must have a diameter smaller than the internal diameter of the microcatheter, and preferably less than about 0.0060 inch (0.152 mm).

The stylet, like the microcatheter, must also be non-toxic and biocompatible, in addition to being rigid enough to reinforce the microcatheter so that it can be inserted through the spinal needle. Generally, the stylet will be a metal wire of suitable diameter, preferably made of stainless steel.

The stylet utilized in the present invention will be a stainless steel wire having an outer diameter of about 0.0025 inch (0.063 mm) to about 0.0035 inch (0.089 mm) with a polytetrafluoroethylene coating of about 0.0010 inch (0.025 mm) to about 0.0020 inch (0.051 mm). Such coated wires are readily available from numerous manufacturers of magnet or motor wires.

In practicing the method of the present invention utilizing the above-described apparatus for the continuous administration of spinal anesthesia, one first inserts the spinal needle (with introducer if desired) into the desired spinal site of the patient (e.g. the L2-3 or L3-4 interspace) until it penetrates the subarachnoid space. Then the apparatus of the present invention, namely the microcatheter with reinforcing stylet, is inserted through the spinal needle and advanced until the inserted end of the microcatheter has projected beyond the needle opening (generally about 2 to 4 cm) into the subarachnoid space. Anesthetic is then administered through the microcatheter as required to achieve and maintain the desired level of spinal blockade.

The anesthetic may be infused through the microcatheter with the stylet still in place provided that there is sufficient clearance between the stylet and the microcatheter internal walls to allow a sufficient volume of anesthetic to pass through. This is practical and advantageous when using, for example, a 32 guage microcatheter, with internal diameter of about 0.0079 inch, and a stylet which has an overall outer diameter of about 0.0045 inch (0.003 inch stainless wire with 0.0015 inch PTFE coating). With the stylet maintained in place, the microcatheter will not kink and form an occlusion, and the difficult step of removing the stylet without accidentally moving the position of the microcatheter is avoided.

Generally, the anesthetic is delivered to the microcatheter via a 3 cc syringe, although a 1 cc syringe can be utilized to increase the infusion rate. A connector is used to couple the syringe to the microcatheter. It is particularly advantageous to use a Tuohy-Borst adapter as the connecting means. Such an adapter is available from Teleflex Medical Inc. of Jaffrey, N.H. and size 20 to 24 guage is particularly suitable for the apparatus of the present invention.

Figure 7:
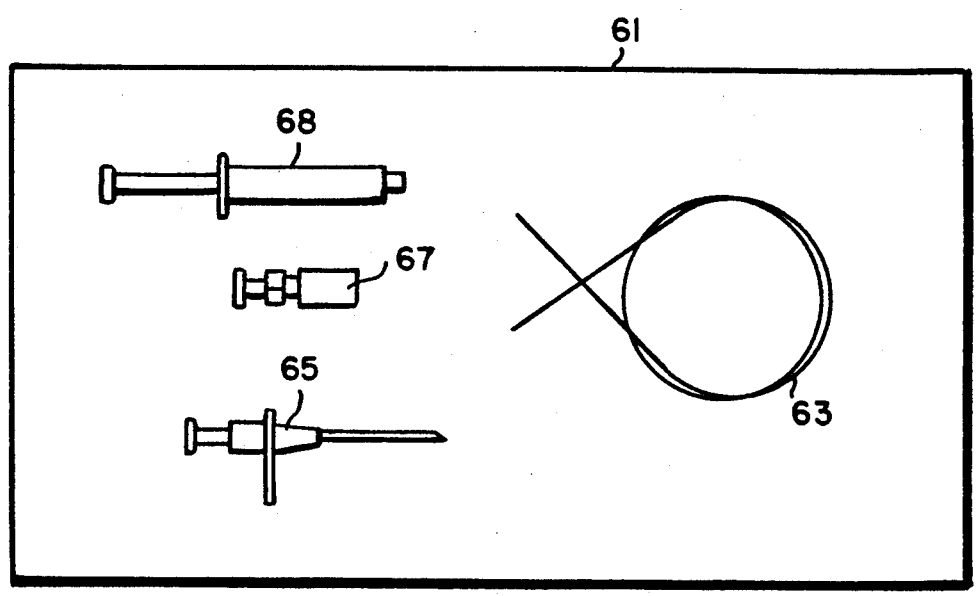
FIG. 7 illustrates a kit of components, including a microcatheter according to the present invention, for facilitating the application of spinal anesthetic.

As illustrated in FIG. 7, the apparatus of the present invention may be advantageously made available to the medical profession in the form of a catheter kit which has been packaged in a sterile, sealed package 61. In addition to the microcatheter with inserted stylet, designated generally by reference character 63, the catheter kit would also advantageously contain a spinal needle 65 of the desired size and a Tuohy-Borst adapter 67. The syringe for delivering the anesthetic, designated by reference character 68, may also be included in the kit.

While the method of the present invention may be practiced with a stylet left in place as described hereinbefore, it may also be advantageous to employ a stylet or similar reinforcing member more permanently fixed in place, e.g. during manufacturing of the microcatheter of the present invention.

One way of making such a reinforced microcatheter is to cement a reinforcing wire within the lumen of the catheter using the same polymer/solvent mixture as is typically used in the manufacture of the tubing described hereinbefore. For example, a reinforced microcatheter useful in the present invention may be fabricated according to the following steps:

1. Copper wire is continuously pulled from a spool through a furnace (500 degrees F.) which oxidizes the surface.
2. The oxidized copper wire is then pulled through a polymer (e.g., polyimide)/solvent mixture and then through a wiping die which controls the amount of polymeric mixture that remains on the copper wire.
3. The coated wire is then pulled through a second furnace which utilizes three temperature zones (approximately 200, 300 and 600 degrees F.) to evaporate the solvent and cure the polymer.
4. Steps 2 and 3 are repeated approximately 8-12 times utilizing successively larger wiping dies until the desired wall thickness is obtained.
5. The coated copper wire is then cut into specified lengths (generally 2-6 feet) and the polymer is stripped from each end, thereby exposing the copper wire.
6. Both ends of the copper wire are grasped and pulled until the copper wire irreversibly stretches and its diameter decreases to the point that the copper wire can be removed from inside the polymeric coating.
7. The polymeric tubing is flushed with nitric acid to remove copper oxide residuals and rinsed with water.
8. The flushed tubing is then placed in an oven to evaporate the water left in the lumen.
9. After the drying procedure, a reinforcement wire (approximately 0.003" diameter) is placed inside the lumen so that it extends beyond both ends of the tubing.
10. A small amount of the polymer/solvent mixture is wicked down each end of the reinforcement wire and the assembly is placed in an oven at approximately 500 degrees F. in order to evaporate the solvent and cure the polymer.
11. After curing, both ends of the catheter are cut so that the reinforcement wire does not extend beyond the polymeric tubing itself.
12. Each catheter assembly is tested for clear passage (lumen patency) by passing filtered air or a liquid through the lumen.

Figure 4:
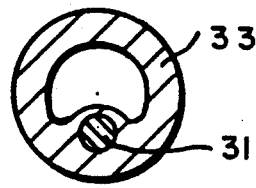
FIG. 4 is a cross-sectional view showing a microcatheter made in accordance with the method of FIG. 3.
Figure 3:
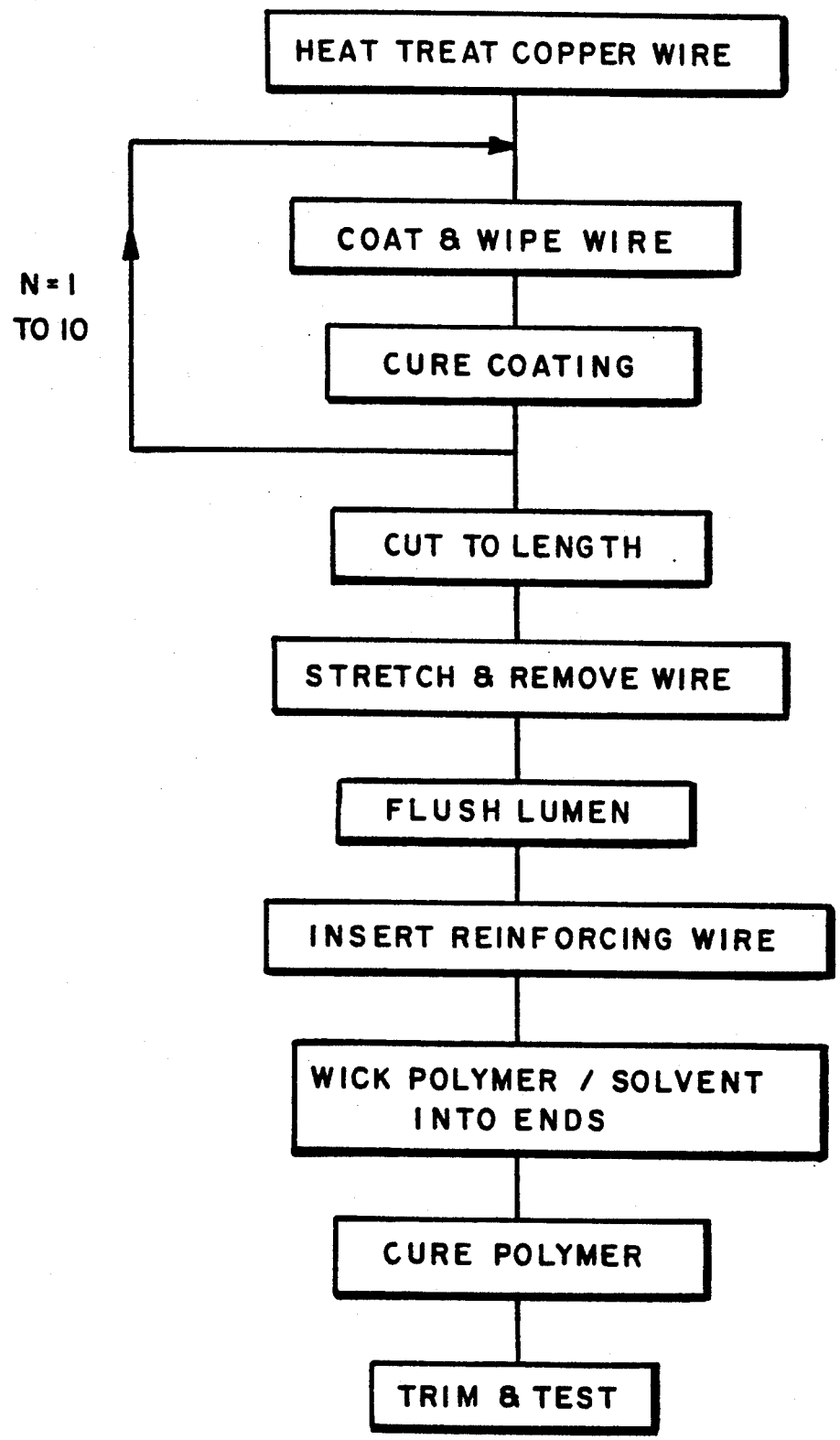
FIG. 3 is a flowchart illustrating a method of making a microcatheter in accordance with the present invention.

These steps are illustrated in FIG. 3 and the resultant structure is illustrated in FIG. 4. As may be seen in FIG. 4, the wicking of an additional increment of polymer/solvent into the lumen of the catheter forms a coating and fillet joining the reinforcing wire, designated by reference character 31 to the previously formed tube 33.

An alternative method of fabricating a reinforced microcatheter is to incorporate a reinforcing wire the wall of the catheter as it is built up in stages. For example, the catheter may be constructed proceeding according to the following steps:

1. Copper wire is continuously pulled from a spool through a furnace (500 degrees F.) which oxidizes the surface.
2. The oxidized copper wire is then pulled through a polymer (e.g., polyimide)/solvent mixture and then through a wiping die which controls the amount of polymeric mixture that remains on the copper wire.
3. The coated wire is then pulled through a second furnace which utilizes three temperature zones (approximately 200, 300 and 600 degrees F.) to evaporate the solvent and cure the polymer.
4. Steps 2 and 3 are repeated approximately 2-3 times utilizing successively larger wiping dies until the desired wall thickness is obtained.
5. The reinforcement member (i.e., 0.003" diameter stainless steel wire) is then fed with the coated copper wire through the polymer/solvent mixture and a specially-profiled wiping die.
6. A solvent evaporation and polymer curing operation like step 3 is performed.
7. Steps 5 and 6 are repeated 6-10 times utilizing successively larger wiping dies until the desired wall thickness is reached.
8. The coated copper wire is then cut into specified lengths (generally 2-6 feet) and the polymer is stripped from each end, thereby exposing the copper wire.
9. Both ends of the copper wire are grasped and pulled until the copper wire irreversibly stretches and its diameter decreases to the point that the copper wire can be removed from inside the polymeric coating.
10. The polymeric tubing is flushed with nitric acid to remove copper oxide residuals and rinsed with water.
11. The flushed tubing is then placed in an oven to evaporate the water left in the lumen.
12. After curing, both ends of the catheter are cut so that the reinforcement wire does not extend beyond the polymeric tubing itself.

Figure 6:
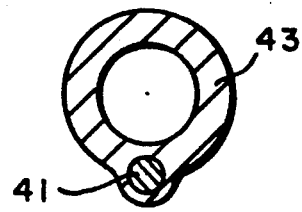
FIG. 6 is a cross-sectional view illustrating a microcatheter made in accordance with the method of FIG. 5.
Figure 5:
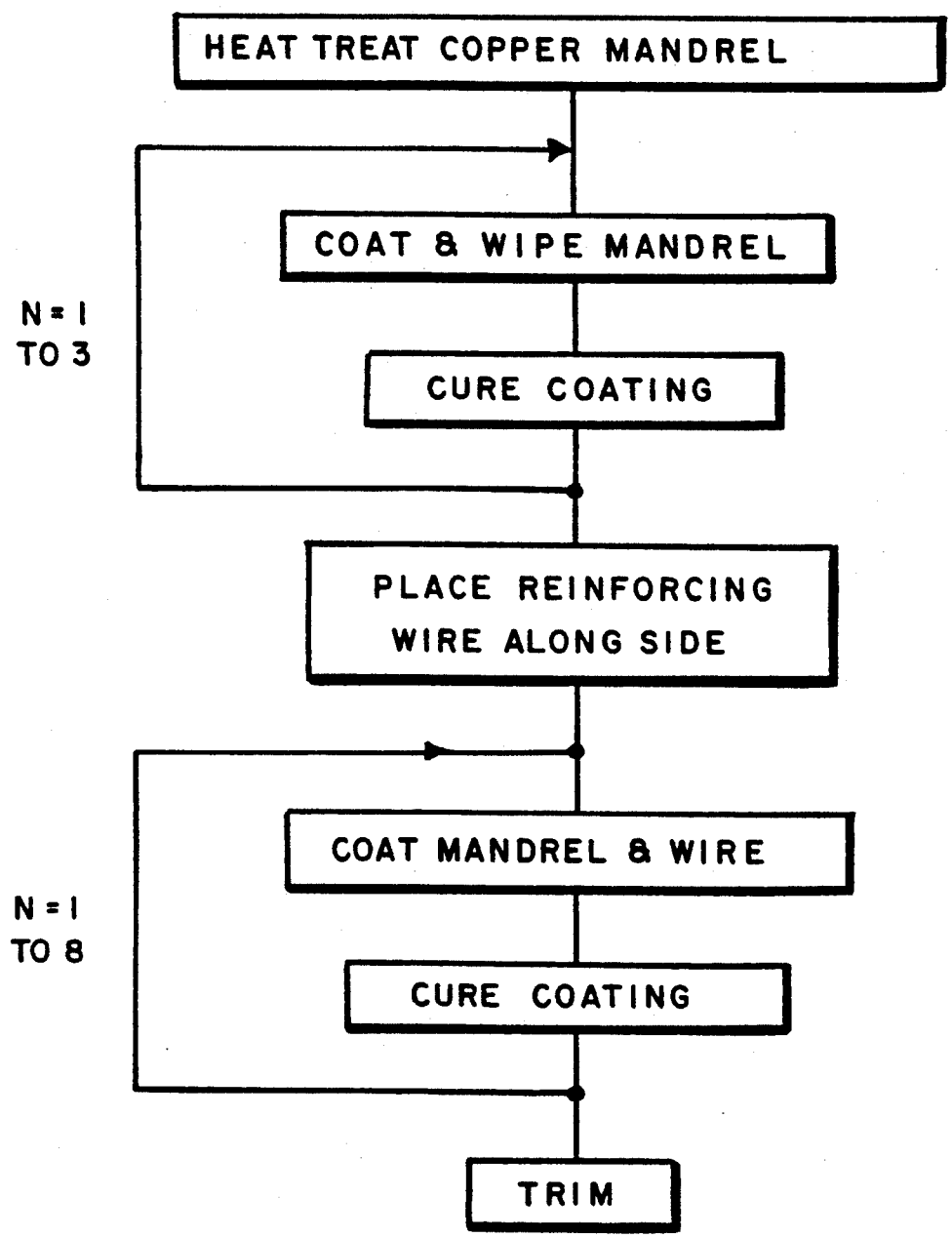
FIG. 5 is a flowchart illustrating an alternative method of making a microcatheter.

These steps are illustrated in FIG. 5 and the resultant structure is illustrated in FIG. 6. As may be seen in FIG. 6, the introduction of the reinforcing wire part way through the series of coating steps which forms the tubing wall causes the reinforcing wire 41 to be incorporated into the wall structure 43 itself.

While the invention has been described with reference to particular materials and methods, it should be apparent that the substitution of equivalent materials or methods may be equally employed and are contemplated hereunder. For example, the apparatus of the present invention may also be utilized for continuous epidural anesthesia as well as the spinal (or peridural) anesthesia described. The invention is thus defined by the following claims.

What is claimed is:

1. A continuous spinal anesthesia administering apparatus comprising a polymeric microcatheter having an external diameter less than about 0.0130 inch (0.330 mm) and further comprising a reinforcing member extending substantially the length of the microcatheter and fixed so that the reinforcing member is maintained within the microcatheter during infusion of the anesthetic.

2. The apparatus according to claim 1 wherein said reinforcing member is bonded to the wall of said microcatheter.

3. The apparatus according to claim 1 wherein said microcatheter has an external diameter of about 0.0085 inch (0.216 mm) to about 0.0107 inch (0.272 mm).

4. The apparatus according to claim 3 wherein said microcatheter has an internal diameter of about 0.0071 inch (0.180 mm) to about 0.0091 inch (0.230 mm).

5. The apparatus according to claim 4 wherein said reinforcing member comprises a stainless steel wire of about 0.0025 inch (0.063 mm) to about 0.0035 inch (0.089 mm) diameter with a fluoropolymer coating of about 0.0010 inch (0.025 mm) to about 0.0020 inch (0.051 mm) thickness.

6. The apparatus according to claim 5 additionally comprising means for connecting said microcatheter to an anesthesia injecting means.

7. The apparatus according to claim 6 wherein said connecting means comprises a Tuohy-Borst adapter.

8. The apparatus according to claim 7 additionally comprising a spinal needle of about 24 gauge (0.508 mm O.D.) to about 26 gauge (0.403 mm O.D.), through which said microcatheter is inserted into a patient.

9. The apparatus according to claims 5, 6, 7 or 8 wherein said microcatheter is fabricated of an aromatic polyimide.

10. The apparatus of claim 1, wherein said reinforcing member has a diameter of less than about 0.006 inch (0.152 mm).

11. The apparatus of claim 1, wherein said reinforcing member comprises a wire having a diameter of about 0.0025 inch (0.063 mm) to about 0.0035 inch (0.089 mm).

12. The apparatus according to claim 1 wherein said reinforcing member is imbedded in the wall of said microcatheter.

13. A catheter kit for the continuous administration of anesthesia to a patient comprising, in a sterile, sealed package; a polymeric microcatheter having a lumen extending throughout its length, the microcatheter including a metal wire reinforcing member extending substantially the length of the microcatheter wholly within the lumen of said microcatheter and fixed so that the reinforcing member is maintained within the microcatheter during infusion of the anesthetic, and a spinal needle through which the said microcatheter may be inserted.

14. The catheter kit according to claim 13 wherein said reinforcing member is bonded to the wall of said microcatheter.

15. The catheter kit according to claim 13 additionally comprising means for connecting said microcatheter to an anesthesia injecting means.

16. The catheter kit according to claim 15 wherein said connecting means comprises a Tuohy-Borst adapter.

17. The catheter kit according to claim 16 wherein said microcatheter has an external diameter of about 0.0085 inch (0.216 mm) to about 0.0107 inch (0.272 mm).

18. The catheter kit according to claim 17 wherein said microcatheter has an internal diameter of about 0.0071 inch (0.180 mm) to about 0.0091 inch (0.230 mm).

19. The catheter kit according to claim 18 wherein said reinforcing member comprises a stainless steel wire of about 0.0025 inch (0.063 mm) to about 0.0035 inch (0.089 mm) diameter with a fluoropolymer coating of about 0.0010 inch (0.025 mm) to about 0.0020 inch (0.051 mm) thickness.

20. The catheter kit according to claim 19 wherein said microcatheter is fabricated of an aromatic polyimide.

21. The kit according to claim 13 wherein said microcatheter has an external diameter less than about 0.0130 inch (0.330 mm).

22. The catheter kit of claim 13, wherein said reinforcing member has a diameter of less than about 0.006 inch (0.152 mm).

23. The catheter kit according to claim 13 wherein said reinforcing member is imbedded in the wall of said microcatheter.

24. A device for administering a medicament to a patient comprising a polymeric microcatheter having an external diameter of less than about 0.0130 inch (0.330 mm) and a metal wire reinforcing member extending substantially the length of the microcatheter and fixed so that the reinforcing member is maintained within the microcatheter during infusion of the anesthetic.

25. The apparatus according to claim 24 wherein said reinforcing member comprises a stainless steel wire having a diameter of about 0.0025 inch (0.063 mm) to about 0.0035 inch (0.089 mm).

26. The apparatus of claim 24, said microcatheter being fabricated of an aromatic polyimide.

27. The apparatus of claim 24, wherein said microcathter is attached to a source of medicament to be administered.

28. The device according to claim 24 wherein said reinforcing member is bonded to the interior of the wall of said microcatheter.

29. The device according to claim 24 wherein said reinforcing member is imbedded in the wall of said microcatheter.

30. The device according to claim 24 in which said reinforcing member is bonded to the wall of said microcatheter.

* * * * *